United States Patent [19]

Lindquist

[11] 3,954,561
[45] May 4, 1976

[54] PROCESS FOR PRODUCING MICROORGANISMS FROM ETHYLENE

[75] Inventor: Robert H. Lindquist, Berkeley, Calif.

[73] Assignee: Chevron Research Company, San Francisco, Calif.

[22] Filed: Sept. 30, 1974

[21] Appl. No.: 510,206

[52] U.S. Cl. .............................. 195/28 R; 195/82
[51] Int. Cl.$^2$ ............................................. C12B 1/00
[58] Field of Search ............ 195/28 R, 49, 82, 96, 195/115; 260/641

[56] References Cited
UNITED STATES PATENTS

| | | | |
|---|---|---|---|
| 2,486,980 | 11/1949 | Robinson | 260/641 |
| 3,546,071 | 12/1970 | Douros et al. | 195/49 |
| 3,681,200 | 8/1972 | Ridgway, Jr. | 195/142 |

Primary Examiner—David M. Naff
Assistant Examiner—R. B. Penland
Attorney, Agent, or Firm—G. F. Magdeburger; R. H. Davies; J. J. De Young

[57] ABSTRACT

The invention is an improvement in the prior art processes for producing a microorganism using ethylene as a carbon source. The improvement comprises:

1. hydrating ethylene by contacting ethylene and water, both being in the vapor phase, with a supported phosphoric acid catalyst to form an aqueous-phase effluent comprising ethanol, diethyl ether, acetaldehyde, dissolved phosphate and water;

2. feeding said effluent without substantial purification to a microorganism fermentation zone; and 3. withdrawing from the fermentation zone an effluent and separating said microorganisms from said effluent and recycling to said hydration zone at least a portion of the unreacted water, ethanol, ether and aldehydes along with excess residual salts.

10 Claims, 1 Drawing Figure

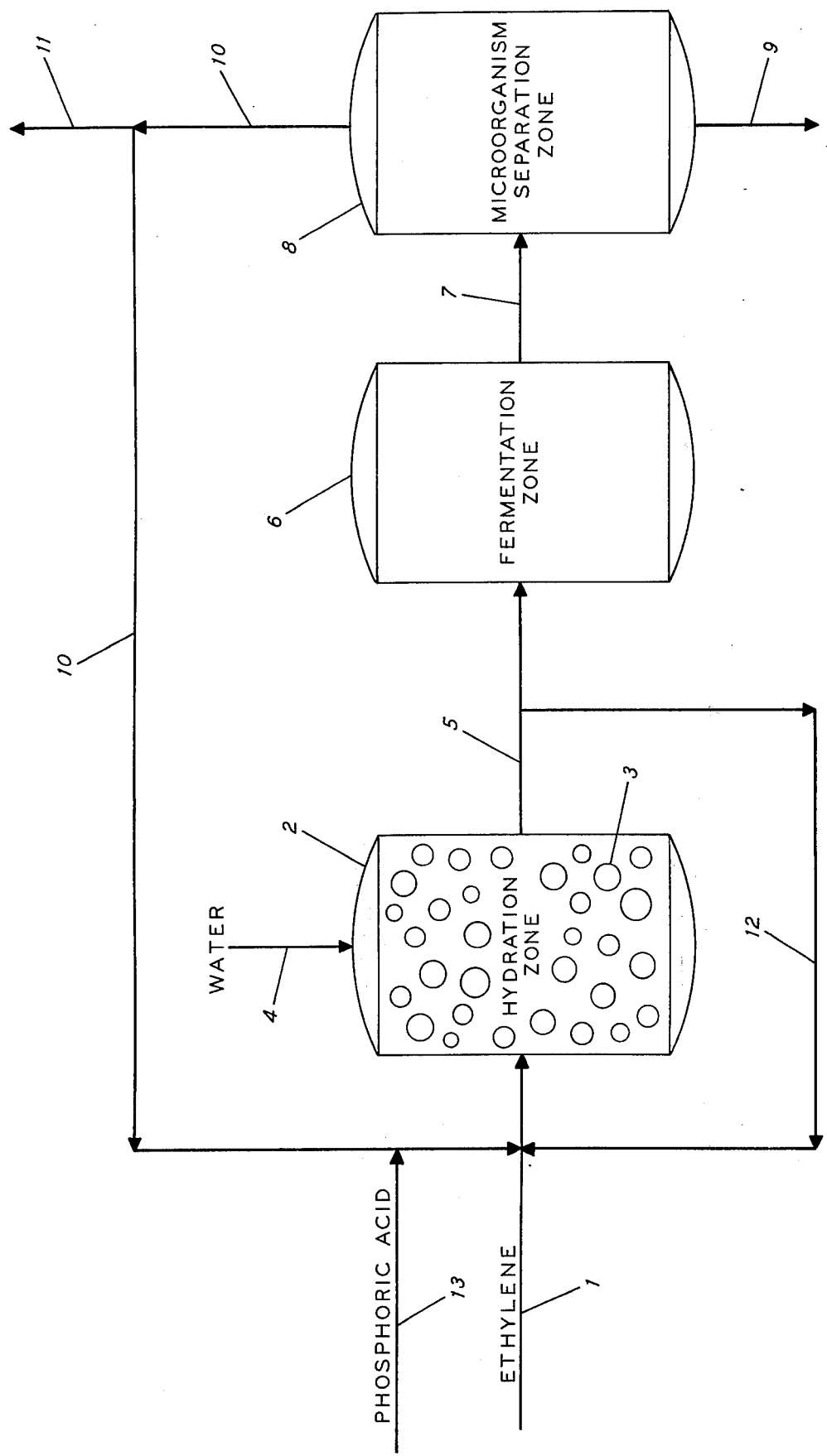

PROCESS FOR PRODUCING MICROORGANISMS FROM ETHYLENE

BACKGROUND OF THE INVENTION

1. Field of the Invention

The invention is directed to a process for producing microorganisms from ethylene. The microorganism, which can be a yeast or bacterium, may be used, for example, as a food or food supplement.

2. Prior Art and Related Disclosures

It is well known in the art that ethanol can be produced by the hydration of ethylene over a phosphoric acid containing catalyst. It is also known that in the hydration of ethylene substantial impurities are also produced, for example diethyl ether and acetaldehyde, and that substantial and costly purification steps are necessary to remove these impurities to produce a concentrated ethanol solution. See, for example, U.S. Pat. No. 2,486,980.

The prior art as exemplified, for example, by the article "Energy Supply and Cell Yield in Aerobically Grown Microorganisms" by E. Hernandes and M. J. Johnson, Journal of Bacteriology, October 1967, Vol. 94, No. 4, pp. 996–1001, discloses growing yeasts, and in particular *Candida utilis*, with ethanol used as the carbon source of the microorganisms.

The prior art further shows in U.S. Pat. No. 3,546,071 oxygenating a petroleum fraction to form oxygenated hydrocarbons, preferably ethanol, and then feeding the oxygenated hydrocarbons to a microorganism, *Micrococcus cerificans*, in the presence of cellulose.

The prior art further discloses in U.S. Pat. No. 3,642,578 that aldehydes are biocidal to microorganisms in the fermentation of methanol and the like.

The prior art also shows in German Patent No. 2,154,091 that an aqueous ethanol solution may be used as a feed for a fermentation zone and that unreacted ethanol may be separated from the effluent and after a suitable sterilization may be recycled to the fermentation zone. Recycle of unreacted substrates is also disclosed in U.S. Pat. No. 3,084,106.

SUMMARY OF THE INVENTION

In an aerobic process for the production of microorganisms in a fermentation zone containing primary and secondary substrates, nitrogen, and essential salts, including phosphates, and wherein said primary substrate consists of ethanol, the improvement comprising:

1. producing a fermentation zone feed containing said primary and secondary substrates by contacting ethylene and water in the vapor phase in a hydration zone with a catalyst comprising phosphoric acid in association with a solid carrier to produce a crude liquid-phase water-ethanol-diethyl ether-acetaldehyde-phosphate-containing mixture;

2. feeding said mixture to said fermentation zone without intervening purification and using said primary and secondary substrates to promote the propagation of said microorganisms;

3. withdrawing from said fermentation zone an effluent and separating said effluent into a first microorganism-rich stream and a second stream containing water and unreacted primary and secondary substrates and excess salts;

4. recycling at least a portion of said second stream to said hydration zone thereby providing a portion of the water needed in said hydration zone and thereby sterilizing said second stream, thus preventing the introduction of microorganism growth inhibitors into said fermentation zone and chemically altering metabolic products from the fermentation zone, particularly amines, so that the water can be reused.

DESCRIPTION OF THE DRAWING

The present invention will be better understood and will be further explained hereinafter by reference to the FIGURE. The FIGURE illustrates one preferred embodiment of the present invention.

DETAILED DESCRIPTION OF THE INVENTION

The present invention is an improved process for producing microorganisms. The processes of the prior art comprise converting ethylene to ethanol, feeding the ethanol and essential nutrients and salts to a fermenter containing microorganisms, maintaining the fermenter under aerobic conditions conducive to producing rapid growth of the microorganisms, and recovering a microorganism product. The prior art further teaches that after removal of the microorganisms one must sterilize the water and unreacted substrate mixture before recycle to the fermentation zone.

Some of the many advantages of the present invention over the prior art methods are: (1) separation and dehydration steps are not needed to recover the ethanol in pure form; (2) the phosphate impurities present in the hydration zone effluent are beneficial to the growth of the microorganism; (3) the diethyl ether, acetaldehyde and other organic impurities present in the hydration zone effluent are utilized as secondary substrate for growth of the microorganism; (4) excess phosphoric acid can be added with the ethylene or to the recycle fermentation broth to maintain catalyst activity as the phosphoric acid is removed with the hydration zone effluent; (5) recycle of the water and unreacted substrate and excess nutrients and salts from the fermentation zone to the hydration zone greatly reduces waste-water-treatment costs, since water is consumed in the hydration reaction; (6) sterilization costs normally associated with the prior art processes are also avoided with recycle to the hydration zone, since the high temperatures in the hydration zone function to sterilize the recycle stream and prevent the buildup of antitoxins or microorganism growth inhibitors in the fermentation zone.

Other advantages of the process of the present invention over the processes of the prior art will become apparent from the description which follows.

Production of Ethylene

Ethylene from any source is usable in the process of the present invention. For example, the ethylene may be produced from a hydrocarbon feedstock containing substantial amounts of saturated hydrocarbons by any of a number of processes; as one example, the hydrocarbon feedstock can be thermally cracked and ethylene can be separated from the effluent from the thermal cracking zone. Alternatively, a hydrocarbon feedstock rich in ethane, propane and/or butane can be dehydrogenated, usually with some accompanying cracking, as, for example, by contacting the ethane-, propane-, and/or butane-rich stream with a dehydrogenation catalyst in a dehydrogenation zone at dehydrogenation conditions. In short, any economically attractive method for producing the ethylene can be utilized.

Recovery of Ethylene

The ethylene used in the process of the present invention can be produced from any of a great number of hydrocarbon feedstocks. The ethylene produced will often be highly contaminated with other hydrocarbons and most often with other olefins. Thus, a separation step will often be needed to separate the ethylene from other impurities. The separation can be carried out by conventional procedures, for example distillation.

Hydration

It is essential to the practice of the present invention that the hydration of ethylene to form ethanol be carried out by contacting ethylene and water, both in the vapor phase, with a catalyst comprising phosphoric acid in association with a solid carrier. This method of hydrating ethylene is known in the prior art and is described, for example, in U.S. Pat. No. 3,232,997 of Wilhelm Ester, the disclosure of which is incorporated herein by reference. As is set out in the Ester patent, the pH value of the crude alcohol may be adjusted by the addition of an alkaline material thereto. The acidity of the crude alcohol is due to phosphoric acid that is removed from the catalyst along with an effluent comprising water, ethanol and impurities, such as acetaldehyde, diethyl ether and the like.

Generally when ethanol is produced by the vapor-phase phosphoric acid-catalyzed hydration of ethylene, the crude effluent typically contains 3 to 20 weight percent ethanol and is carefully purified, e.g., hydrogenated and then distilled or extracted, to prepare relatively water-free and oxygenated organic-impurity-free, for example 190 proof, ethanol. The hydrogenation in particular is a very expensive process. It is an advantage of the present invention that the crude effluent from the hydration is used as a feed for microorganisms without any substantial reduction of the amount of oxygenated organic impurities. The dissolved phosphate and most of the organic impurities present in the crude effluent are, in fact, often desirable, since they serve as secondary substrates and nutrients for the growth of the microorganism.

It is desirable, in order to reduce corrosion of equipment, to adjust the pH of the crude effluent by the addition of an alkaline material thereto. In a preferred embodiment of the present invention, the pH of the crude effluent is adjusted using ammonium and/or potassium hydroxide. This is desirable, since both ammonia and potassium in limited quantities are essential to the growth of microorganisms.

The hydration zone conditions are well known in the art and typically include a temperature in the range 240° to 320°C. or higher. This high temperature, relative to that of the fermentation zone, serves the important function of sterilizing the feed to the fermentation zone and thus preventing the buildup of microorganism growth inhibitors.

Microorganisms

The term "microorganism" is used herein to include all yeasts or bacteria as described below.

A. Yeast

The term "yeast" is used herein in a broad sense to include all yeasts that can grow under aerobic conditions using ethanol as a feed. A yeast of any of the 39 known genera of yeasts may be used. The terminology used to describe the yeast herein is based upon the classification published in "The Yeasts, a Taxonomic Study," editor J. Lodder (1970).

Thus, the yeast which may be produced by the improved process of the present invention is selected from the genera Brettanomyces, Bullera, Candida, Citromyces, Coccidiascus, Cryptococcus, Debaryomyces, Dekkera, Endomycopsis, Hanseniaspora, Hansenula, Kloeckera, Kluyveromyces, Leucosporidium, Lipomyces, Lodderomyces, Metschnikowia, Nadsonia, Nematospora, Oosporidium, Pachysolen, Pichia, Pityrosporum, Rhodosporidium, Rhodotorula, Saccharomyces, Saccharomycodes, Saccharomycopsis, Schizoblastosporion, Schizosaccharomyces, Schwanniomyces, Sporidiobolus, Sporobolomyces, Sterigmatomyces, Torulopsis, Trichosporon, Trigonopsis, Wickerhamia and Wingea. Preferably the yeast is selected from the genera Candida, Kluyveromyces and Saccharomyces. More preferably the yeast is selected from the group consisting of *Candida utilis* var. *thermophilia, C. utilis* var. *major, C. arborea, C. japonica, C. tropicalis, Rhodotorula glutinis, Saccharomyces cerevisiae, S. cerevisiae* var. *ellipsoideus, S. carlsbergensis* and *Kluyveromyces fragilis*.

The yeast produced by the process of the present invention is useful as a food or food supplement and most useful as a food supplement in animal feeds. The yeast produced by the process of the present invention is an aerobic yeast; that is, it grows in the presence of an oxygen source.

B. Bacteria

The term "bacteria" is used herein in a broad sense to include all bacteria that can grow under aerobic conditions using ethanol as a feed. Included within the term bacteria are bacteria of the class Schizomycetes, including the subclasses Chlamydnobacteriales, Myxobacteriales, Actinomycetales, Mycoplasmatales, Spirochaetales, Beggiatoales, Pseudomonadales, Hyphomicrobiales, Caryophonales and Eubacteriales. The bacteria produced by the process of the present invention are useful as a food or food supplement and most useful as a food supplement in animal feeds. The bacteria produced by the process of the present invention are aerobic bacteria, that is, they grow in the presence of an oxygen source.

Growth of Microorganism

The microorganism of the present invention is grown in a fermentor under aerobic conditions. A microorganism-water inoculant is combined with a fermentation broth containing water and essential salts in a fermentor maintained at a temperature and pH conducive to rapid growth of the particular microorganism being produced. The crude ethanol-containing effluent produced by the hydration step disclosed above is used as a carbon source, preferably as the major carbon source, and still more preferably as substantially the sole carbon source for the microorganism; thus, the crude ethanol-containing effluent is introduced into the fermentor. The ethanol in the hydration zone effluent serves as the primary substrate for the microorganism and the diethyl ether, acetaldehyde and other oxygenated impurities in the crude effluent serve as secondary substrates for growth of the microorganism. Preferably the concentration of ethanol in the fermentation broth is maintained below about 1 percent by weight.

The fermentor operates aerobically in that an oxygen source is present; that is, either oxygen itself or an oxygen source may be supplied to the broth wherein the microorganism is cultivated in any form in which it may be readily assimilated by the microorganism. It is also possible to use oxygencontaining compounds as the oxygen source so long as the oxygen-containing compounds do not seriously inhibit microorganism growth. A typical way of supplying oxygen is to supply it as an oxygen-containing gas, e.g., air or commercial oxygen gas, at atmospheric or elevated pressure. Oxygen-enriched air may also be used. It is preferred that between about 0.05 and 20, and more preferably from about 0.05 to about 5, volumes of air be supplied to the fermentor per volume of liquid in the fermentor per minute.

It is essential that nitrogen be supplied to the fermentor for the microorganism to grow. Any nitrogen source, that is, any compound which releases nitrogen in a form suitable for use by the microorganism, is satisfactory. Examples of suitable nitrogen compounds include amino acids, proteins, urea, asparagine, enzyme-digested proteins, acid-hydrolyzed proteins, yeast extract and the like. Other suitable nitrogen compounds are ammonia, ammonium salts as in ammonium hydroxide, ammonium phosphate, ammonium citrate, ammonium sulfate, ammonium nitrate and ammonium acid pyrophosphate, and nitric acid or its salts. It is convenient to supply nitrogen as ammonium hydroxide, ammonium phosphate, ammonium acid phosphate or simply as gaseous ammonia. As has been pointed out above, a particularly desirable method of introducing the ammonia is to use ammonium hydroxide to adjust the pH of the crude water-ethanol-phosphate effluent obtained from the hydration of ethylene. Even when the pH of the water-ethanol-phosphate effluent is adjusted with ammonium hydroxide, it may be desirable to further adjust the pH of the fermentation broth by the addition of ammonia or ammonium hydroxide thereto.

Certain inorganic salts must also be supplied in the required amounts to the fermentor so that proper growth of the microorganism results. The essential salts may include, for example, potassium, sodium, iron, magnesium, calcium, manganese, phosphorus, and the like. Generally the essential salts are supplied in the form of water-soluble salts.

Usable potassium salts include potassium phosphate, potassium chloride, potassium sulfate, potassium citrate, potassium acetate and potassium nitrate. Phosphorus and iron can be supplied, for example, in the form of iron phosphate. Most of the phosphorus, however, is usually supplied as ammonium phosphates. Clearly, ammonium phosphates serve as sources of both nitrogen and phosphorus. At least a portion of the phosphate is introduced as part of the crude water-ethanol-phosphate effluent from the hydration of ethylene. As was stated above, in a preferred embodiment of the present invention at least a portion of the potassium can be supplied by using potassium hydroxide or combinations of potassium and ammonium hydroxides to neutralize the ethanol-containing crude effluent from the hydration of ethylene.

Preferably the fermentation is carried out with yeast at a pH from about 3 to about 7; more preferably the pH of the incubation is in the range from about 4 to about 6; and still more preferably the pH range is from about 4.5 to about 5.5. With bacteria, the pH ranges are 4–9, preferably 5.5–8, and more preferably 6.5–7.5. The preferred temperature range for both yeast and bacteria is 80° to 100°F.

The amount of nitrogen supplied to the broth is generally from about 0.04 to about 0.30 and preferably from about 0.1 to about 0.2 grams of nitrogen per gram of dried microorganism produced. This amount of nitrogen is equivalent to about 0.05 to about 0.3 weight percent and preferably from about 0.1 to about 0.2 weight percent nitrogen, based on the total broth.

Recovery of the Microorganism

The microorganism may be harvested from the broth by, for example, centrifugation, filtration, or the like, with or without the use of filtration aids and may then be dried as, for example, by spray drying, drum drying, tumble drying or the like. When the microorganism is a yeast it is pale in color, has little odor, and is relatively bland tasting.

Recycle of the Fermentation Broth to the Hydration Zone

The fermentation broth contains water, ethanol, small amounts of secondary substrates and residual quantities of other essential salts and nutrients. The prior art processes, for example German Pat. No. 2,154,091, teach that a portion of the broth can be recirculated to the fermentation zone after a suitable sterilization step. The broth must be sterilized in order to prevent the buildup of bactericides or toxins which would either kill or inhibit the growth of the desired microorganisms. Furthermore, water is a byproduct of the fermentation step and in prior art processes, with recycle to the fermentation zone, a portion of this water must be removed in order to maintain the desired concentration in the fermentation zone. Thus, removal of water is a substantial burden on prior art processes. Furthermore, because of the impurities present in this waste water, subsequent cleanup also adds substantially to the costs of prior art processes.

These sterilization, waste-water-separation and cleanup burdens are substantially reduced in the process of the present invention, wherein at least a portion of the separated liquid broth is recycled to the hydration zone wherein the broth is sterilized and the water produced in the fermentation zone is consumed in the hydration zone. From 20 to 100 volume percent of the separated liquid is recycled, and preferably 50–95 volume percent is recycled. A portion of the separated liquid broth can also be bled from the system so as to prevent the buildup of detrimental impurities such as chloride ions, as disclosed in German Patent Publication No. 2,154,091.

Because of the organic compounds present in the recycle stream, particularly amines and other metabolic fermentation zone products, phosphoric acid is preferably added to this recycle stream. The phosphoric acid reacts with these compounds, thus allowing reuse of what would normally be waste water. For example, the amines will react with the acid, forming phosphates, which are essential to the fermentation reaction. Sufficient excess phosphoric acid is added to the recycle stream or directly to the hydration zone to replace that portion of the phosphoric acid catalyst removed with the hydration zone effluent. Sufficient phosphoric acid is added so as to maintain a high level of conversion of ethylene in the hydration zone. The amount of phosphoric acid added is determined and controlled by monitoring the hydration zone reaction rate and by conventional pH measurements of the recycle stream and hydration zone effluent. Thus, in addition to the high temperatures of the hydration zone, the phosphoric acid also helps to prevent the introduction of microorganism growth inhibitors into the fermentation zone.

Preferably the amount of nitrogen compounds added to the hydration zone effluent is carefully controlled so that excess phosphoric acid additions are not necessary to replace the acid removed with the hydration zone effluent. Excess ammonia can readily be removed from the recycle stream with a simple flash step or distillation. This excess ammonia may then be recycled and added to the fermentation zone feed, thus preventing any buildup of excess phosphates formed by the reaction of phosphoric acid and ammonia.

DETAILED DESCRIPTION OF THE DRAWING

Ethylene is conducted via line 1 to hydration zone 2. Hydration zone 2 contains catalyst 3 comprising phosphoric acid in association with a solid carrier. Water is introduced to hydration zone 2 via line 4. The water and ethylene supplied to hydration zone 2 are in the vapor phase when they contact the catalyst 3. The liquid-phase product produced in hydration zone 2 is conducted via line 5 to fermentor 6 and the gaseous-phase unreacted ethylene is recycled to the hydration zone via line 12. The fermentation apparatus is conventional in the art as illustrated, for example, in U.S. Pat. No. 3,681,200. At least a portion of the microorganism produced in fermentor 6 is passsed via line 7 to separation zone 8 and the microorganisms are recovered as a product via line 9. Equipment for centrifuging and drying the microorganisms is not illustrated because of its conventional character. The separated fermentation broth is recycled via line 10 to the hydration zone. A portion of the broth is disposed of via line 11. Heat-exchange equipment for cooling the fermentation broth, cooling the hydration-zone product and heating the recycle sream 10 is not shown because of its conventional nature. Liquid phosphoric acid is added to the recycle stream 10 via line 13. Sufficient excess phosphoric acid is added to replace the phosphoric acid catalyst removed with the hydration zone effluent.

The present invention will be more readily understood by reference to the following examples, which illustrate specific embodiments thereof.

EXAMPLES

EXAMPLE 1

In a 1-liter glass fermentor approximately 3 inches-ID by 16 inches high, in which agitation was accomplished by means of paddles affixed to a vertical stirrer shaft, said glass fermentor having indentations in the glass walls at the same level as the paddles to act as baffles, was placed 926 grams of a solution having the following composition:

|  | Grams/Liter |
| --- | --- |
| $(NH_4)_2SO_4$ | 1.0 |
| $NH_4Cl$ | 1.28 |
| $KH_2PO_4$ | 2.74 |
| $MgSO_4.7H_2O$ | 1.36 |
| $CaCl_2.2H_2O$ | 0.20 |
| $NaCl$ | 0.20 |
| $FeSO_4.7H_2O$ | $20 \times 10^{-3}$ |
| $ZnSO_4.7H_2O$ | $1.0 \times 10^{-3}$ |
| $MnSO_4.H_2O$ | $1.0 \times 10^{-3}$ |
| $CuSO_4.5H_2O$ | $0.2 \times 10^{-3}$ |
| $Co(NO_3)_2.6H_2O$ | $0.2 \times 10^{-3}$ |
| $Na_2B_4O_7.10H_2O$ | $0.2 \times 10^{-3}$ |

-continued

|  | Grams/Liter |
| --- | --- |
| $Na_2MoO_4.2H_2O$ | $4.0 \times 10^{-3}$ |

To this was added 74 grams of an inoculum consisting of a paste of living *Candida utilis* var. major (NRRL Y-900) which had been separated from a previous day's run by centrifugation and held overnight in a refrigerator. The paste had a cell density of 215 grams/kilogram.

The fermentor was equipped with a gas inlet, a paddle-type foam-breaker in the gas exit line with a liquid return line to the fermentor, a membrane-type oxygen probe for monitoring dissolved oxygen, and a pH probe connected so that the ammonia-containing feed was metered into the fermentor by a motor-driven syringe pump at the rate required to maintain the pH from about 5.5 to about 5.8. Constant temperature was maintained by an electrically heated belt around the outside of the fermentor and a cooling coil on the inside through which cooling water was automatically circulated as required.

A simulated impure ethanol feed was prepared having the following composition. The amounts of organic impurities in the feed were deliberately exaggerated over that which would be present if the feed came from phosphoric acid-catalyzed hydration of ethylene.

| Constituent | Wt.% |
| --- | --- |
| Diethyl ether | 0.4 |
| Isobutyladehyde | 0.046 |
| Methylethylketone | 0.004 |
| t-Butyl alcohol | 0.019 |
| Valderaldehyde | 0.142 |
| 3-Methyl-2-butanol | 0.071 |
| sec-Butyl alcohol | 0.73 |
| Acetaldehyde | 0.16 |
| Ethyl alcohol | 15.5 |
| Balance — water | |

Because a slight oily film appeared, this solution was extracted with 100 ml of mixed hexanes in a separatory funnel, and the hexane layer discarded. To 921 grams of the resulting aqueous solution, 33.4 grams of concentrated aqueous ammonia was added.

After the initial charge to the fermentor was heated to a temperature of 89°F, the stirrer and syringe pump were started and oxygen was introduced at a rate which was increased from about 0.25 at the start to about 0.75 volumes of gas per volume of fermentor liquid per minute at the end. The simulated feed was also introduced at a rate to maintain the pH within the range from about 5.5 to about 5.8. The initial cell density of 15 increased to 30 at the end of the run. A total of 33.49 grams of alcohol was fed during the 6-hour run, of which 29.10 grams was consumed. Cells in the inoculum had a dry weight of 14.98 grams, and the total cells recovered weighed (dry weight) 35.97 grams. Therefore, the yield of dried cells on ethanol consumed was 72%.

EXAMPLE 2

Apparatus and run conditions were similar to those in Example 1. The simulated crude ethanol feed had the following composition:

|  | Wt.% |
|---|---|
| Water | 83.4 |
| Ethanol | 15.5 |
| Isopropanol | 0.23 |
| t-Butanol | 0.05 |
| sec-Butanol | 0.18 |
| Diethyl ether | 0.455 |
| Acetaldehyde | 0.18 |

133 grams of *Candida utilis* (NRRL Y-900) inoculum having a cell density of 15.8 g/kg was used, and the total starting weight of the charge was 803 grams. The final weight was 867 grams. The starting and final cell densities were 2.6 and 15.2 g/kg, respectively. 16.3 grams of ethanol was fed and 15.7 grams consumed. 2.1 grams of cells were charged and 13.2 grams recovered for a dry weight yield of 71%.

EXAMPLE 3

A series of shake-flask tests was made in which *Candida utilis* (NRRL Y-900) was grown on ethanol containing at least 5% of one of the following possible impurities: diethyl ether, acetaldehyde, isopropanol, n-butanol, 2-butanol, and crotonaldehyde. In each case growth was obtained.

EXAMPLE 4

A series of shake-flask tests was carried out in which a variety of microorganisms was grown in the medium given in Table I.

TABLE I

Medium for Yeast and Bacteria Growth

| Chemical | Yeast, g/l of Solution | Bacteria, g/l of Solution | g/l of dilute Ethanol Feed |
|---|---|---|---|
| $(NH_4)_2SO_4$ | 1.00 | — |  |
| $NH_4Cl$ | 1.28 | 0.50 |  |
| $KH_2PO_4$ | 2.74 | — |  |
| $MgSO_4 \cdot 7H_2O$ | 1.36 | 0.80 |  |
| $CaCl_2 \cdot 2H_2O$ | 0.20 | 0.04 |  |
| NaCl | 0.20 | — |  |
| $FeSO_4 \cdot 7H_2O$* | 0.02 | 0.02 |  |
| $ZnSO_4 \cdot 7H_2O$ | 0.0010 | 0.0010 |  |
| $MnSO_4 \cdot H_2O$ | 0.0010 | 0.0010 |  |
| $CuSO_4 \cdot 5H_2O$ | 0.0002 | 0.0002 |  |
| $Co(NO_3)_2 \cdot 6H_2O$ | 0.0002 | 0.0002 |  |
| $Na_2B_4O_7 \cdot 10H_2O$ | 0.0002 | 0.0002 |  |
| $Na_2MoO_4 \cdot 2H_2O$ | 0.004 | 0.0040 |  |
| $(NaPO_3)_6$ | — | 1.60 |  |
| $K_2HPO_4$ | — | 3.00 |  |
| $NH_4H_2PO_4$ | — | 1.60 |  |
| Ethanol — 95% |  |  | 15.40 |
| Crotonaldehyde |  |  | 0.22 |
| Diethyl Ether |  |  | 0.36 |
| n-Butyl Alcohol |  |  | 0.21 |
| Acetaldehyde |  |  | 0.17 |
| Water |  |  | 84.53 |

*Added as EDTA complex (ethylenedinitrile) tetraacetic acid disodium salt

Growth rate was measured by increase in turbidity using a Klett-Summerson Photoelectric Colorimeter. In each case growth took place as shown by the increase in turbidity in corrected Klett units. Results are given in Table II.

TABLE II

Growth of Microorganisms on Ethanol-Based Nutrient

| Microorganism | Incubation Time, Hrs. | Turbidity Klett Units Initial | Final |
|---|---|---|---|
| *Saccharomyces cerevisiae* (ATCC 2601) | 52.5 | 11 | 63 |
| *Saccharomyces cerevisiae* (NRRL Y-2753) | 52.5 | 11 | 52 |
| *Candida arborea* (ATCC 20176) | 52.5 | 10 | 87 |
| *Candida japonica* (ATCC 14473) | 52.5 | 3 | 65 |
| *Candida tropicalis* (ATCC 9968) | 52.5 | 4 | 49 |
| *Candida utilis* (NRRL Y-1084) | 32 | 11 | 92 |
| *Candida utilis* (NRRL Y-793) | 32 | 13 | 84 |
| *Candida utilis* (NRRL Y-900) | 32 | 8 | 83 |
| *Rhodotorula glutinis* (ATCC 10788) | 52 | 10 | 81 |
| *Acinetobacter calcoaceticus* (ATCC 21716) | 46.5 | 0 | 297 |

What is claimed is:

1. In an aerobic process for the production of microorganisms in a fermentation zone containing primary and secondary substrates, nitrogen, and essential salts, including phosphate, and wherein said primary substrate consists of ethanol, the improvement comprising:
   1. producing a fermentation zone feed containing primary and secondary substrates by contacting ethylene and water in the vapor phase in a hydration zone with a catalyst comprising phosphoric acid in association with a solid carrier to produce a crude liquid-phase water-ethanol-diethyl ether-acetaldehydephosphate-containing mixture;
   2. feeding said mixture to said fermentation zone without intervening purification and using said primary and secondary substrates to promote the propagation of said microorganisms;
   3. withdrawing from said fermentation zone an effluent and separating said effluent into a first microorganism-rich stream and a second stream containing water and unreacted substrate; and
   4. recycling at least a portion of said second stream to said hydration zone.

2. A process as in claim 1 including as an added step adjusting the pH of the crude water-ethanol-diethyl ether-acetaldehyde-phosphate-containing effluent by the addition thereto of ammonium hydroxide or potassium hydroxide.

3. A process as in claim 1 wherein the microorganism comprises a yeast selected from the genera Brettanomyces, Bullera, Candida, Citromyces, Coccidiascus, Cryptococcus, Debaryomyces, Dekkera, Endomycopsis, Hanseniaspora, Hansenula, Kloekera, Kluyveromyces, Leucosporidium, Lipomyces, Lodderomyces, Metschnikowia, Nadsonia, Nematospora, Oosporidium, Pachysolen, Pichia, Pityrosporum, Rhodosporidium, Rhodotorula, Saccharomyces, Saccharomycodes, Saccharomycopsis, Schizoblastosporion, Schizosaccharomyces, Schwanniomyces, Sporidiobolus, Sporobolomyces, Sterigmatomyces, Torulopsis, Trichosporon, Trigonopsis, Wickerhamia and Wingea.

4. A process as in claim 3 wherein the yeast is selected from the genera Candida, Kluyveromyces, Rhodotorula and Saccharomyces.

5. A process as in claim 4 wherein the yeast is selected from the group consisting of *Candida utilis* var.

*thermophilia, C. utilis* var. *major, C. arborea, C. japonica, C. tropicalia, Rhodotorula glutinis, Saccharomyces cerevisiae, S. cerevisiae* var. *ellipsoideus, S. carlsbergensis* and *Kluyveromyces fragilis*.

6. A process as in claim 5 wherein the yeast comprises *Candida utilis* var. *major*.

7. A process as in claim 3 wherein the conditions conducive to producing rapid growth of the yeast include a pH within the range from about 3 to about 7 and a temperature within the range from about 80° to about 100°F.

8. A process as in claim 1 wherein the essential salts include phosphorus, potassium and magnesium compounds.

9. A process as in claim 1 wherein sufficient excess phosphoric acid is added to said recycle stream to replace the phosphoric acid catalyst removed with the hydration zone effluent.

10. The process of claim 9 wherein 50 to 95 volume percent of said second stream is recycled to said hydration zone.

* * * * *